(12) United States Patent
Giulianotti et al.

(10) Patent No.: US 10,799,727 B2
(45) Date of Patent: Oct. 13, 2020

(54) HELMET FOR ANESTHESIA

(71) Applicant: THE BOARD OF TRUSTEES OF THE UNIVERSITY OF ILLINOIS, Urbana, IL (US)

(72) Inventors: Pier Giulianotti, Urbana, IL (US); Arturo Vittori, Urbana, IL (US); Andreas Vogler, Urbana, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 809 days.

(21) Appl. No.: 14/897,642

(22) PCT Filed: Jun. 13, 2014

(86) PCT No.: PCT/US2014/042281
§ 371 (c)(1),
(2) Date: Dec. 10, 2015

(87) PCT Pub. No.: WO2014/201338
PCT Pub. Date: Dec. 18, 2014

(65) Prior Publication Data
US 2016/0107006 A1 Apr. 21, 2016

Related U.S. Application Data

(60) Provisional application No. 61/834,510, filed on Jun. 13, 2013.

(51) Int. Cl.
*A62B 18/04* (2006.01)
*A61M 16/06* (2006.01)
(Continued)

(52) U.S. Cl.
CPC .......... *A62B 18/04* (2013.01); *A61G 13/1215* (2013.01); *A61M 16/0627* (2014.02);
(Continued)

(58) Field of Classification Search
CPC .. A61M 16/009; A61M 16/0627; A62B 18/04
See application file for complete search history.

(56) References Cited

U.S. PATENT DOCUMENTS

| 456,687 A | * | 7/1891 | Bader | A62B 18/04 |
| | | | | 128/201.16 |
| 1,264,706 A | * | 4/1918 | Stallworth | A62B 18/04 |
| | | | | 128/201.24 |

(Continued)

FOREIGN PATENT DOCUMENTS

| CN | 203168090 | 9/2013 |
| GB | 828731 A | 2/1960 |

(Continued)

OTHER PUBLICATIONS

International Preliminary Report on Patentability for PCT/2014/042279 filed Jun. 13, 2014 on behalf of the Board of Trustees of the University of Illinois. Dated Dec. 4, 2015.
(Continued)

*Primary Examiner* — Victoria Murphy
(74) *Attorney, Agent, or Firm* — Steinfl + Bruno, LLP

(57) ABSTRACT

A helmet for anesthesia, adapted to keep confined anesthetic gases and to administer them in a non-invasive fashion to a patient laying on an operating table, allowing to provide oxygen and/or anesthetic gases through tubes and fast access to the patient's head in case of emergency is described. The helmet has a lower half-shell and an upper half-shell, the lower half-shell being anatomically shaped to receive and support the nape and the neck of the laying patient, the upper half-shell and the lower half-shell having fastening means for fastening one to the other and being configured to be fitted one to the other and to the neck or torso of the patient to form a substantially airtight enclosure for enclosing head of the patient, at least one inlet port for gas supply and at
(Continued)

least one outlet port for gas evacuation being on the lower half-shell and/or the upper half-shell.

15 Claims, 3 Drawing Sheets

(51) Int. Cl.
   *A61G 13/12* (2006.01)
   *A62B 18/10* (2006.01)
   *A61M 16/04* (2006.01)
   *A61M 16/01* (2006.01)
(52) U.S. Cl.
   CPC ............. *A62B 18/10* (2013.01); *A61M 16/01* (2013.01); *A61M 16/0409* (2014.02); *A61M 2202/0208* (2013.01); *A61M 2202/0241* (2013.01)

(56) References Cited

U.S. PATENT DOCUMENTS

| | | | | |
|---|---|---|---|---|
| 1,344,349 A * | 6/1920 | Arthur | ............... | A62B 18/04 379/430 |
| 2,366,904 A * | 1/1945 | Haugh | ............... | A61G 10/04 128/206.24 |
| 2,418,473 A * | 4/1947 | Lambertsen | ........... | A61G 10/04 128/205.26 |
| 2,508,050 A * | 5/1950 | Valente | ............... | A61G 10/04 128/205.26 |
| 2,543,426 A * | 2/1951 | Terhaar | ............... | A61H 31/02 600/22 |
| 2,742,900 A * | 4/1956 | Giorgio | ............. | A61M 16/0627 128/201.23 |
| 2,785,674 A * | 3/1957 | Wong | ............... | A61M 16/0627 128/201.23 |
| 2,954,562 A * | 10/1960 | Krupp | ............... | A62B 17/00 2/2.14 |
| 3,239,843 A | 3/1966 | Lobelle | | |
| 3,362,403 A * | 1/1968 | Fleming | ............... | A42B 3/32 128/201.24 |
| 3,473,165 A * | 10/1969 | Gran | ............... | A62B 18/04 2/422 |
| 3,552,391 A * | 1/1971 | Deaton | ............... | A61G 10/04 128/205.26 |
| 3,783,863 A | 1/1974 | Kliever | | |
| 3,859,993 A * | 1/1975 | Bitner | ............... | A61G 10/04 128/847 |
| 3,889,670 A * | 6/1975 | Loveland | ............. | A61G 10/04 128/203.12 |
| 4,181,129 A * | 1/1980 | Canneto | ............... | A61G 10/04 128/205.26 |
| 4,215,437 A * | 8/1980 | Kao | ............... | A62B 18/04 2/424 |
| 4,236,514 A * | 12/1980 | Moretti | ............... | A62B 17/04 128/201.23 |
| 4,407,280 A * | 10/1983 | Trammell | ............. | A61M 16/06 128/205.19 |
| 4,433,988 A * | 2/1984 | Hinchliffe | ............ | A62B 18/04 2/425 |
| 4,550,713 A * | 11/1985 | Hyman | ............... | A61F 9/007 128/849 |
| 4,620,538 A * | 11/1986 | Koegel | ........... | A61M 16/0627 128/201.23 |
| 4,683,880 A * | 8/1987 | Werjefelt | ............... | A62B 15/00 128/201.23 |
| 4,750,474 A | 6/1988 | Dukhan et al. | | |
| 4,763,664 A * | 8/1988 | Merilainen | .......... | A61B 5/0806 128/201.23 |
| 4,832,042 A * | 5/1989 | Poppendiek | ...... | A61M 16/0627 600/543 |
| 5,322,245 A | 6/1994 | Bassick | | |
| 5,335,653 A * | 8/1994 | Blomqvist | ............... | A61B 5/083 128/200.24 |
| 5,360,001 A * | 11/1994 | Brill | ............... | A61G 10/026 128/202.12 |
| 5,370,110 A * | 12/1994 | Corn | ............... | A61M 16/009 128/201.22 |
| 5,526,818 A * | 6/1996 | Ruismaki | ............... | A61B 5/097 128/201.23 |
| 5,566,668 A * | 10/1996 | Jesadanont | ............ | A62B 17/04 128/201.22 |
| 5,626,151 A | 5/1997 | Linden | | |
| 5,694,929 A * | 12/1997 | Christopher | ....... | A61M 16/0488 128/205.25 |
| 5,819,728 A * | 10/1998 | Ritchie | ................. | A62B 17/04 128/201.23 |
| 5,964,217 A * | 10/1999 | Christopher | ....... | A61M 16/0488 128/200.26 |
| 5,975,081 A | 11/1999 | Hood et al. | | |
| 6,047,203 A | 4/2000 | Sackner et al. | | |
| 6,073,284 A | 6/2000 | Borders | | |
| 6,076,524 A * | 6/2000 | Corn | ............... | A61M 16/009 128/205.12 |
| 6,112,333 A | 9/2000 | Mazzei | | |
| 6,155,260 A | 12/2000 | Lavin et al. | | |
| 6,245,028 B1 | 6/2001 | Furst et al. | | |
| 6,321,764 B1 | 11/2001 | Gauger et al. | | |
| 6,371,110 B1 * | 4/2002 | Peterson | ............... | A62B 18/084 128/202.27 |
| 6,401,278 B1 | 6/2002 | Hayes et al. | | |
| 6,443,148 B1 * | 9/2002 | Rodocker | ........... | A61G 10/026 128/202.12 |
| 6,460,187 B1 | 10/2002 | Siegel | | |
| 6,493,890 B2 | 12/2002 | Smeed | | |
| 6,792,623 B2 * | 9/2004 | Luppi | ............... | A61M 16/06 128/200.28 |
| 7,296,570 B2 * | 11/2007 | Hutchinson | ............... | A61F 7/02 128/201.26 |
| 7,540,283 B2 * | 6/2009 | Loori | ............... | A61M 35/30 128/202.12 |
| 7,677,245 B2 * | 3/2010 | Borsari | ............... | A61M 16/06 128/201.29 |
| 8,033,281 B2 | 10/2011 | Kneale et al. | | |
| 8,291,907 B2 * | 10/2012 | Kuhlmann | ........... | A61M 16/06 128/207.11 |
| 8,365,734 B1 * | 2/2013 | Lehman | ........... | A61M 16/0078 128/200.24 |
| 8,555,439 B2 * | 10/2013 | Soto | ............... | A61G 13/121 128/869 |
| 10,105,272 B2 | 10/2018 | Giulianotti et al. | | |
| 10,130,127 B2 | 11/2018 | Giulianotti et al. | | |
| 10,307,217 B2 * | 6/2019 | Sparkuhl | ............ | A61M 16/06 |
| 10,368,949 B2 | 8/2019 | Giulianotti et al. | | |
| 2002/0138905 A1 | 10/2002 | Bartlett et al. | | |
| 2003/0075174 A1 * | 4/2003 | Shahaf | ............... | A61M 16/06 128/201.25 |
| 2003/0097060 A1 | 5/2003 | Yanof et al. | | |
| 2003/0127093 A1 * | 7/2003 | Maniscalco | ....... | A61M 16/0627 128/201.23 |
| 2004/0040064 A1 | 3/2004 | Mah et al. | | |
| 2004/0267145 A1 | 12/2004 | David et al. | | |
| 2005/0028811 A1 * | 2/2005 | Nelson | ............... | A61M 16/06 128/200.11 |
| 2005/0056279 A1 * | 3/2005 | Linton | ............... | A61G 10/026 128/202.12 |
| 2006/0137686 A1 * | 6/2006 | Macris | ............... | A61M 16/06 128/201.22 |
| 2006/0150335 A1 | 7/2006 | Dankbaar et al. | | |
| 2006/0150984 A1 * | 7/2006 | Ferguson | ............... | A61F 5/3707 128/846 |
| 2007/0113856 A1 * | 5/2007 | Acker | ............... | A61M 16/0627 128/207.14 |
| 2007/0272244 A1 * | 11/2007 | Witmer | ............... | A62B 17/04 128/205.25 |
| 2009/0235928 A1 * | 9/2009 | Borsari | ............... | A61M 16/06 128/201.23 |
| 2010/0031443 A1 | 2/2010 | Georgiev et al. | | |
| 2010/0108067 A1 * | 5/2010 | Walker | ............... | A62B 18/084 128/205.24 |
| 2010/0162488 A1 | 7/2010 | Dahlin et al. | | |

(56) References Cited

U.S. PATENT DOCUMENTS

| | | | |
|---|---|---|---|
| 2010/0242150 A1 | 9/2010 | Trouillot | |
| 2011/0036358 A1* | 2/2011 | Mattalino | A61F 13/00987 |
| | | | 128/857 |
| 2011/0076771 A1 | 3/2011 | Gabriele et al. | |
| 2011/0240017 A1* | 10/2011 | Butler | A61G 10/04 |
| | | | 128/201.25 |
| 2011/0289644 A1 | 12/2011 | Beshlian | |
| 2012/0136231 A1 | 5/2012 | Markel | |
| 2012/0146784 A1 | 6/2012 | Hines et al. | |
| 2012/0158074 A1 | 6/2012 | Hall | |
| 2012/0246795 A1 | 10/2012 | Scheffler et al. | |
| 2012/0285448 A1* | 11/2012 | Dugan | A61M 16/0694 |
| | | | 128/202.16 |
| 2012/0285455 A1* | 11/2012 | Varga | A61M 16/0051 |
| | | | 128/204.21 |
| 2012/0289838 A1* | 11/2012 | Varga | A61M 16/06 |
| | | | 600/473 |
| 2012/0289851 A1* | 11/2012 | Varga | A61B 5/0836 |
| | | | 600/532 |
| 2013/0085510 A1 | 4/2013 | Stefanchik et al. | |
| 2013/0178870 A1 | 7/2013 | Schena | |
| 2014/0014099 A1* | 1/2014 | Elliott | A62B 9/006 |
| | | | 128/201.23 |
| 2014/0073996 A1* | 3/2014 | Jaguan | A61N 5/0618 |
| | | | 601/15 |
| 2014/0331999 A1* | 11/2014 | Rossi | A61M 16/0627 |
| | | | 128/202.27 |
| 2015/0272687 A1* | 10/2015 | Sparkuhl | A61M 16/1075 |
| | | | 128/857 |
| 2015/0290480 A1* | 10/2015 | Ritchie | A61M 16/06 |
| | | | 128/201.23 |
| 2016/0120723 A1 | 5/2016 | Giulianotti et al. | |
| 2016/0128399 A1 | 5/2016 | Giulianotti et al. | |
| 2016/0135905 A1 | 5/2016 | Giulianotti et al. | |
| 2016/0193485 A1* | 7/2016 | Izz | A62B 18/04 |
| | | | 128/201.25 |
| 2017/0065016 A1* | 3/2017 | Chuback | A63B 71/12 |

FOREIGN PATENT DOCUMENTS

| | | |
|---|---|---|
| JP | 2006280534 | 10/2006 |
| JP | 2007175266 | 7/2007 |
| KR | 10-2011-030038 A | 3/2011 |
| WO | 1992/18084 A1 | 10/1992 |
| WO | 1999/029235 A | 6/1999 |
| WO | 0000152 | 1/2000 |
| WO | 03/097145 | 11/2003 |
| WO | 2005/102084 A1 | 11/2005 |
| WO | 2007/128571 | 11/2007 |

OTHER PUBLICATIONS

International Preliminary Report on Patentability for PCT/2014/042277 filed Jun. 13, 2014 on behalf of the Board of Trustees of the University of Illinois. Dated Dec. 15, 2015.
International Search Report for PCT/US2014/042279 filed Jun. 13, 2014 on behalf of the Board of Trustees of the University of Illinois. Dated Nov. 4, 2014.
Written Opinion for PCT/US2014/042279 filed Jun. 13, 2014 on behalf of the Board of Trustees of the University of Illinois. Dated Nov. 4, 2014.
International Search Report for PCT/US2014/042286 filed Jun. 13, 2014 on behalf of the Board of Trustees of the University of Illinois. Dated Nov. 4, 2014.
Written Opinion for PCT/US2014/042286 filed Jun. 13, 2014 on behalf of the Board of Trustees of the University of Illinois. Dated Nov. 4, 2014.
International Preliminary Report on Patentability for PCT/US2014/042286 filed Jun. 13, 2014 on behalf of the Board of Trustees of the University of Illinois. Dated Nov. 30, 2015.
International Search Report and Written Opinion for PCT/US2014/042277 filed Jun. 13, 2014 on behalf of the Board of Trustees of the University of Illinois. Dated Nov. 7, 2014.
International Search Report and Written Opinion for PCT/US2014/042281 filed Jun. 13, 2014 on behalf of the Board of Trustees of the University of Illinois. Dated Oct. 20, 2014.
International Preliminary Report on Patentability for PCT/US2014/042281 filed Jun. 13, 2014 on behalf of the Board of Trustees of the University of Illinois. Dated Jun. 26, 2015.
Corrected International Preliminary Report on Patentability for International Application No. PCT/US2014/042279 filed Jun. 13, 2014 on behalf of the Board of Trustees of the University of Illinois. Dated Jan. 29, 2016.
Final Office Action for U.S. Appl. No. 14/897,638 filed Dec. 10, 2015 on behalf of the Board of Trustees of the University of Illinois. Dated Mar. 12, 2018. 7 pages.
Non-Final Office Action for U.S. Appl. No. 14/897.638 filed Dec. 10, 2015 on behalf of the Board of Trustees of the University of Illinois. Dated Oct. 23, 2017. 14 pages.
Notice of Allowance for U.S. Appl. No, 14/897,638 filed Dec. 10, 2015 on behalf of the Board of Trustees of the University of Illinois. Dated Jul. 12, 2018. 5 pages.
Notice of Allowance for U.S. Appl. No. 14/897,639 filed Dec. 10, 2015 on behalf of the Board of Trustees of the University of Illinois. Dated Apr. 23, 2019. 12 pages.
Notice of Allowance for U.S. Appl. No, 14/897,640 filed Dec. 10, 2015 on behalf of the Board of Trustees of the University of Illinois. Dated Aug. 13, 2018. 7 pages.

\* cited by examiner

HELMET FOR ANESTHESIA

CROSS REFERENCE TO RELATED APPLICATIONS

The present application is the national stage entry of International Application No. PCT/US2014/042281, filed on Jun. 13, 2014, which claims priority to U.S. Provisional Application 61/834,510 filed on Jun. 13, 2013, which is incorporated herein by reference in its entirety.

TECHNICAL FIELD

The present disclosure relates to a helmet for anesthesia to be worn by a patient laying upon an operating table.

BACKGROUND

Tracheal intubation is a medical procedure used in anesthesia for surgery patients to ventilate the lungs while preventing the leakage of anesthetic gases into the operating room where it could affect the personnel. However, it is invasive and extremely uncomfortable for the patient.

In order to solve this problem, helmets for artificial respiration have been proposed in literature. The PCT publication WO 2007/128571 discloses a helmet having collar means for air-tight application to the neck. The PCT publication WO 03/097145 discloses a helmet for artificial respiration without the aid of tracheal tubes, having a collar made of a rigid ring for air-tight application to the patient's neck. The U.S. Pat. No. 2,742,900 discloses an anesthetic feeder for children in the form of a space helmet comprising a cylindrical body to enclose the patient's head and neck and a plurality of indentations at the base of the helmet making a loose fit with the general contour of the patient's shoulders.

Of course it is possible to use a mask, though leakage of anesthetic gas in the room may be relevant if the mask is not pressed against the face of the patient. This may be done by placing an elastic around the head of the patient to be operated. Unfortunately, if the head or the neck of the patient has undergone to a trauma, it cannot be moved. Therefore it is not possible to use the helmets disclosed in the above prior documents and, when anesthesia is provided with a mask, an assistant is dedicated to keep and gently press the mask against the patient's face. The effective ventilation of the lungs can also be negatively affected by edemas, rotation of patient tongue, and the leak of gas(es) that decrease ventilation pressure.

There exists an unmet need for technology to safely and comfortably administer anesthetic gases to a patient undergoing a surgical procedure while simultaneously preventing escape of gases into the operating room.

SUMMARY

A helmet for anesthesia, adapted to keep confined anesthetic gases and to administer them in a non-invasive fashion to a patient laying on an operating table, has been found. The helmet, according to an embodiment of the present disclosure, permits to provide oxygen and/or anesthetic gases through tubes and fast access to the patient's head in case of emergency because it comprises a lower half-shell and an upper half-shell, the lower half-shell being anatomically shaped to receive and support the nape and the neck of the laying patient, the upper half-shell and the lower half-shell having fastening means for fastening one to the other and being configured to be fitted one to the other and to the neck or torso of the patient to form a substantially airtight enclosure for enclosing the head of the patient, at least one inlet port for gas supply and at least one outlet port for gas evacuation being defined on the lower half-shell and/or the upper half-shell.

In one embodiment, the lower half-shell and the upper half-shell are hinged together.

An operating table, according to an embodiment of the present disclosure, comprises a helmet as defined above and means for securing in a removable manner the lower half-shell of the helmet to a laying surface of the operating table.

The claims as filed are integral part of this specification and are herein incorporated by reference.

DETAILED DESCRIPTION

Figure 1:
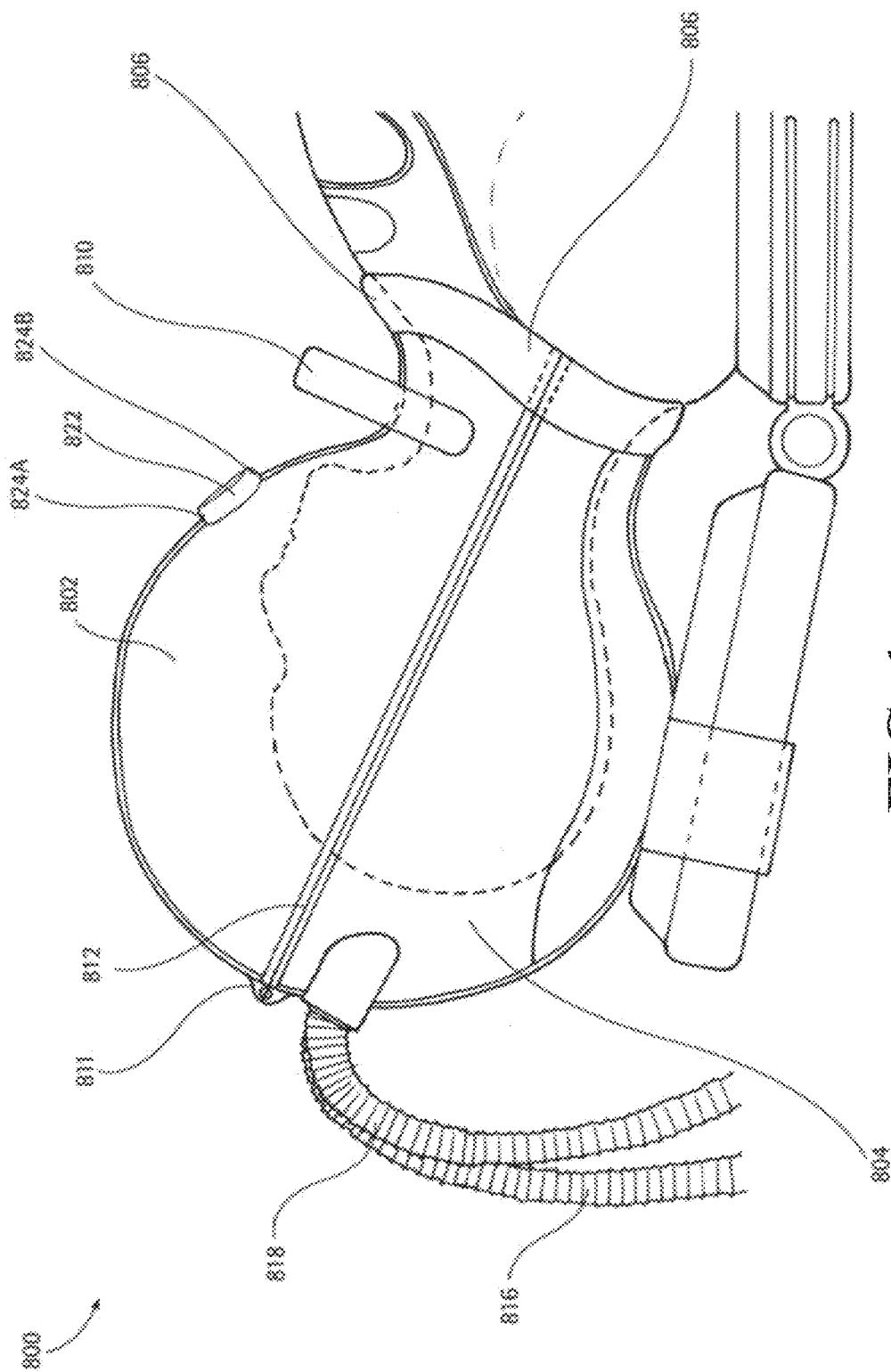
FIG. 1 shows a helmet according to an embodiment, the lower half-shell of which is secured to an operating table to support the nape and the neck of a laying patient.
Figure 2:
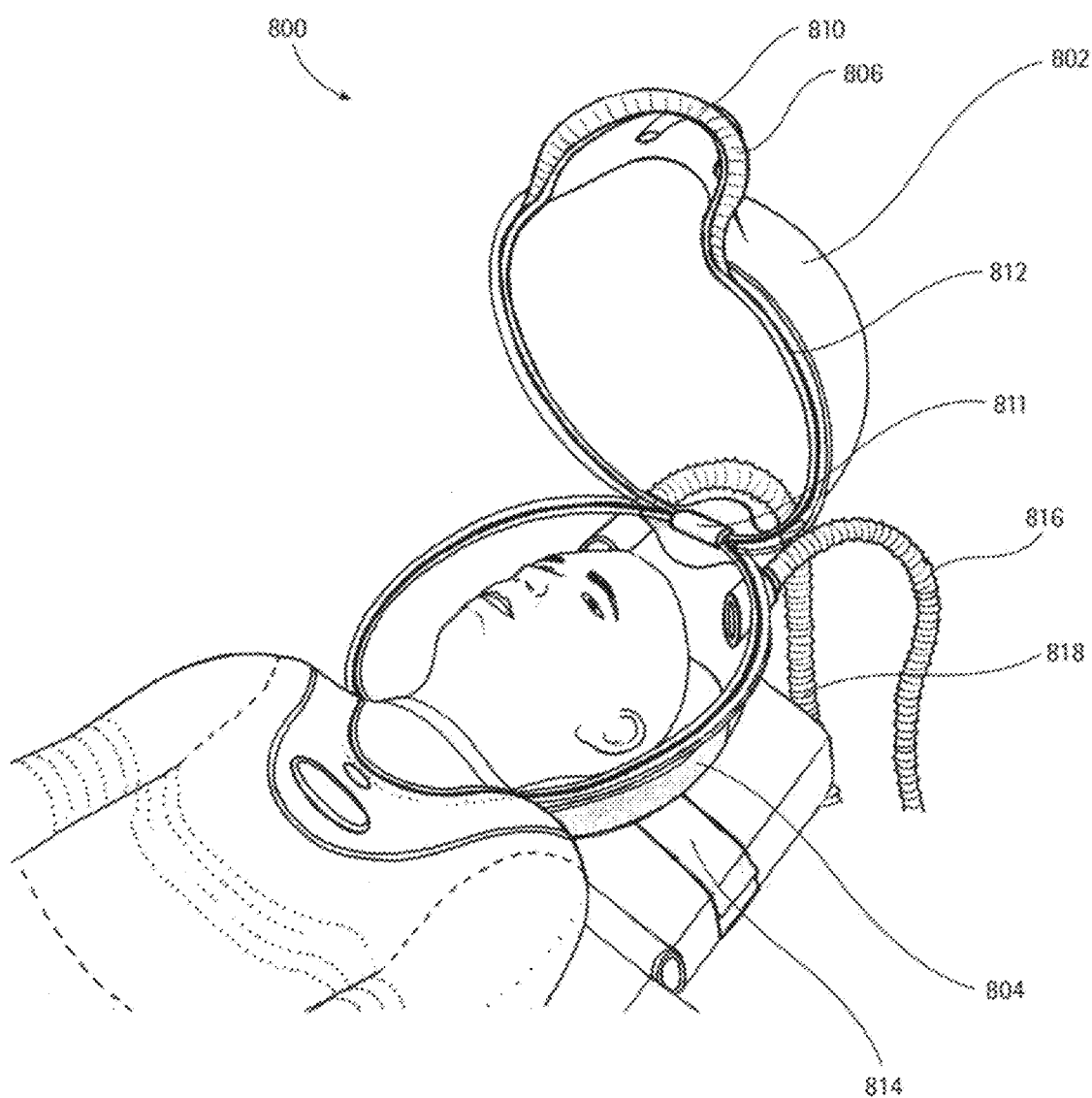
FIG. 2 depicts a patient under anesthesia wearing a helmet, according to an embodiment of the present disclosure, enclosing his head.

An embodiment of the helmet for anesthesia of the present disclosure is depicted in FIGS. 1 and 2. It mainly comprises a lower half-shell 804 anatomically shaped to receive and support the nape and the neck of a laying patient, an upper half-shell 802 designed such to be fitted to the lower half-shell 804 to the neck or torso of the patient, and at least one inlet port for supplying gas and at least one outlet port for evacuating gas through and inlet tube 816 and an outlet tube 818.

In the depicted embodiment, inlet and outlet ports are defined on the lower half-shell 804, but it is possible to define them also on the upper half-shell 802.

According to an embodiment of the present disclosure, the head of the patient is accommodated on the lower half-shell 804 of the helmet whilst the helmet is opened, and the upper half-shell 802 is closed over the lower half-shell 804 to enclose the head of the patient. With the helmet, according to an embodiment of the present disclosure, the head of the patient may be enclosed for anesthesia or freed to the open air without moving the head or the neck, as it is highly recommendable when treating traumatized patients.

The helmet may be made of gas impermeable transparent material. When the helmet is closed, the upper half-shell 802 and lower half-shell 804 match to form a substantially airtight seal in order to prevent the escape of the anesthetic gas. This may be accomplished by a variety of means, for example by an airtight shaped fitting of the contact edges of the upper and lower half-shells, or by coating the contact edge of either or both of the upper and lower half-shells with a material adapted to form an airtight seal, such as for example a rubber O-ring seal, or by fixing an airtight gasket 812, as shown in FIG. 1, to the upper half-shell (or to the lower half-shell).

In one embodiment, the helmet has a substantially spherical shape and the upper half-shell 802 and lower half-shell 804 are fitted to one another around the circumference of the spherical shape and in a plane that is substantially parallel with the operating table.

In one embodiment, the helmet further comprises means 814 for securing the lower half-shell to the operating table. Such means may include, for example, straps or any of a variety of fasteners such as snaps, hook and loop (Velcro™) fasteners, and the like. As an option, the lower half-shell 804 of the helmet may constitute a headrest of an operating table so as to lay thereon a patient to be operated.

In one embodiment, the helmet has an anatomically shaped portion is designed to form an airtight seal to the neck or torso of the patient. This may be accomplished, for example, by means of an airtight flap 806 that seals around the neck of the patient. As an alternative, the helmet may also be sealed to a covering that encloses the torso of the patient. An adapted covering is disclosed for example in U.S. provisional patent application No. 61/834,506, incorporated herein by reference in its entirety.

The upper and lower half-shells of the helmet may be secured to one another by any of a variety of fasteners, hinges or combinations thereof. The fasteners are conveniently designed for allowing in emergency situations to open quickly the helmet without having to move the head of the patient.

In one embodiment, the upper half-shell 802 is joined to the lower half-shell 804 by a hinge 811 and optionally by one or more fasteners (not shown in the figures). The upper half-shell 802 may further comprise a handle 810 for easy opening and removal of the helmet, if necessary.

As shown in the figure, the lower half-shell 804 of the helmet may comprise one or more inlet ports for introducing anesthetic gases and one or more outlet ports for evacuating gases. The ports are designed for securing the hoses for introducing or aspirating gases to/from the helmet. For example, the ports may comprise a simple opening comprising an airtight flap or gasket through which the hoses may be inserted into the helmet.

As an alternative, the ports may comprise a nipple on the exterior surface of the helmet to which the hoses may be fitted and optionally secured by a clamp.

In one embodiment, the inlet ports and/or the outlet ports may further comprise a valve(s) to control supply and aspiration of anesthetic gases. The valve(s) may be opened and closed manually or automatically. In one embodiment, the valve(s) for introduction of the anesthetic gases is(are) automatically shut when the helmet is opened.

Figure 3:
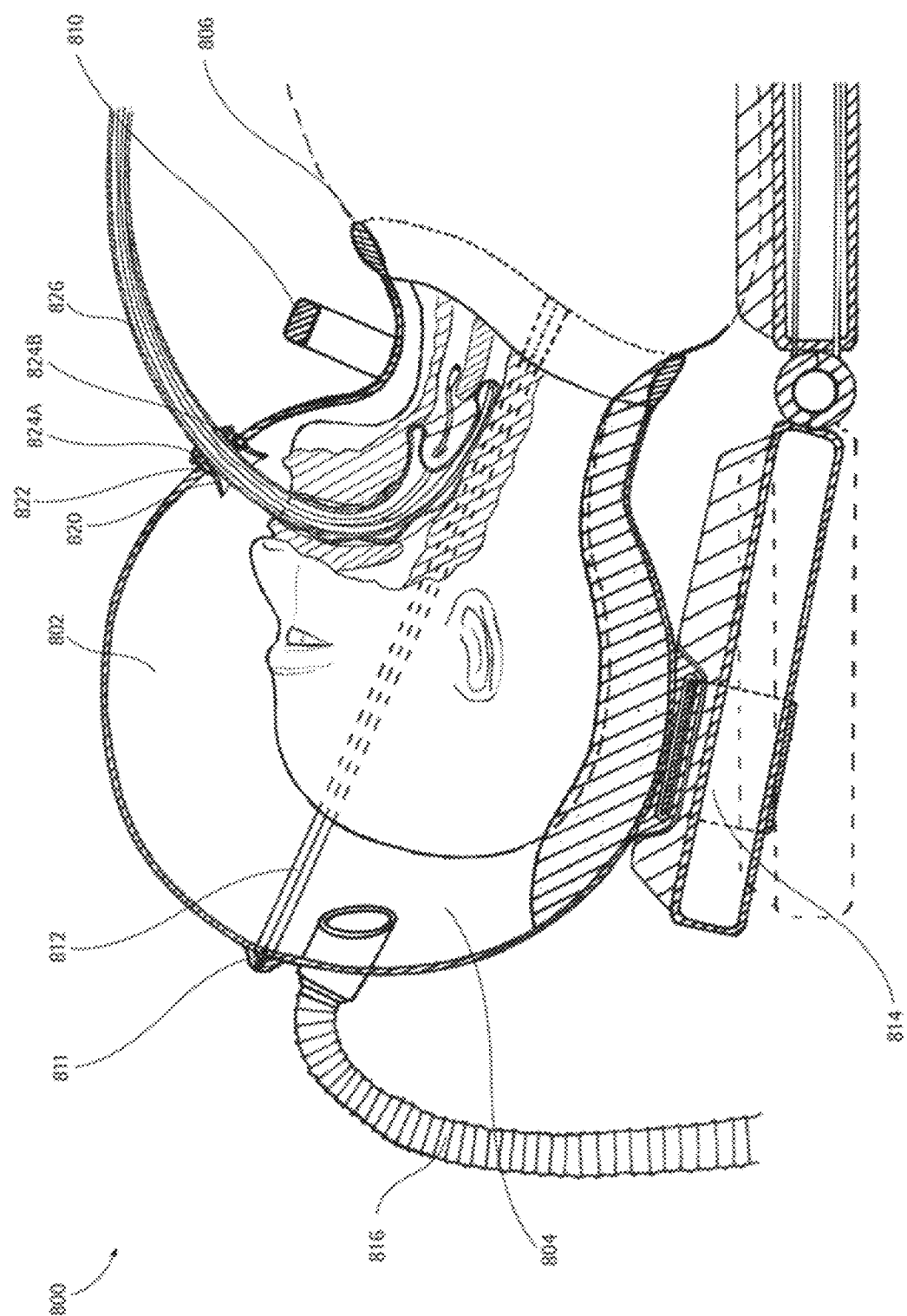
FIG. 3 is a partial cross section of the helmet of FIG. 1 showing a laryngeal mask fitted in an aperture formed in the upper half-shell of the helmet and guided by way of an annular wall surrounding the aperture.

As shown in FIG. 1 and in the partial cross section of FIG. 3, an aperture is formed in the upper half-shell 802 of the helmet. The aperture is closed by a flexible membrane 820 so as to maintain tightness of the helmet. Around the aperture an annular wall 822 is formed, which may be used to fit and guide a laryngeal mask for patient intubation as schematically shown in FIG. 3. As shown in FIG. 3, upon insertion of the laryngeal mask the valve 820 is opened and the mask 826 is guided by the annular wall e.g. at 824A and 824B. Tightness of the helmet is ensured by the contact between the valve 820 and mask 826.

It is understood that the foregoing detailed description is merely illustrative and it is not to be taken as a limitation upon the scope of embodiments according to the present disclosure, which is defined solely by the appended claims and their equivalents. Various changes and modifications to the disclosed embodiments will be apparent to those skilled in the art.

Embodiments

1. A transparent helmet to be worn by a patient on an operating table during a surgical procedure comprising:

a) an upper half-shell; and
b) a lower half-shell, comprising one or more ports for gas supply and one or more ports for gas evacuation,
wherein said upper half-shell and said lower half-shell are fitted to one another and to the neck or torso of the patient to form an airtight enclosure for the head of the patient and are secured to one another by one or more fasteners.

2. The helmet of embodiment 1 further comprising an airtight gasket between said upper and lower half-shells.

3. The helmet of embodiment 2 that is substantially spherical in shape.

4. The helmet of embodiment 3 wherein the upper half-shell and lower half-shell of said helmet are fitted to one another around the circumference of the spherical shape and in a plane that is substantially parallel with the operating table.

5. The helmet of embodiment 1 wherein the upper half-shell and lower half-shell of said helmet are joined by a hinge.

6. The helmet of embodiment 5 wherein said upper half-shell further comprises a handle.

7. The helmet of embodiment 1 wherein said ports further comprise a valve.

8. The helmet of embodiment 7 wherein said valve on said gas supply port further comprises means for automatically closing said valve when the helmet is opened.

9. The helmet of embodiment 1 further comprising means for fastening said lower half-shell to the operating table.

The invention claimed is:

1. A helmet for anesthesia adapted to be worn by a patient laying on an operating table, comprising:
a lower half-shell;
an upper half-shell; and
an anatomically shaped portion attached to said upper half-shell and configured to form an airtight seal to a neck or a torso of the patient,
said lower half-shell being anatomically shaped and configured to receive and support a nape and a rear part of the neck or the torso leaving free a front part of a head and of the neck or the torso and being anatomically shaped such that said lower half-shell is configured to accommodate the head of the patient laying on the operating table,
said upper half-shell being anatomically shaped and configured to cover the front part of the head and of the neck or the torso of the laying patient,
said upper half-shell and said lower half-shell having first fasteners for fastening said upper half-shell to said lower half-shell,
said upper half-shell and said lower half-shell being configured to be fitted together and to the neck or the torso of the patient to form a substantially airtight enclosure configured for enclosing the head of the patient,
said upper half-shell and said lower half-shell forming a substantially spherical shape when fitted together,
said upper half-shell and said lower half-shell being fitted together around a circumference of the substantially spherical shape,
wherein at least one inlet port for supplying gas and at least one outlet port for evacuating gas are defined on said lower half-shell and/or said upper half-shell,
said upper half-shell having an aperture closed by a flexible membrane so as to maintain the substantial airtight enclosure of the helmet, said aperture and said flexible membrane being configured to allow insertion of a laryngeal mask for patient intubation and the flexible membrane being configured to maintain the substantial airtight enclosure of the helmet by contacting the laryngeal mask, said upper half-shell having an annular wall, formed around said aperture, said annular wall configured to fit and guide the laryngeal mask for the patient intubation, wherein the helmet is configured to assume a closed position, when edges of said upper half-shell are brought to match onto corresponding edges of said lower half-shell to form a substantially airtight seal in order to prevent escape of gas, and configured to assume an opened position when said edges of said upper half-shell are detached from said corresponding edges of said lower half-shell, leaving free the front part of the head and of the neck or torso, said upper half-shell and said lower half-shell being shaped and configured to enclose together the head of the patient in said substantially airtight enclosure surrounding the neck or the torso of the laying patient when in the closed position, and are configured to free the head and the neck or the torso of the laying patient in the opened position allowing the laying patient to exit from said lower half-shell and to remove the helmet by raising the head, or to free the head of the patient to open air without moving the head or the neck;

wherein said helmet further comprises second fasteners directly fixed to said lower half-shell configured for securing said lower half-shell to said operating table.

2. The helmet of claim 1, wherein said first fasteners comprise a hinge and wherein said lower half-shell and said upper half-shell are connected by said hinge on an outside of the helmet and are configured such that the helmet is placed in the opened position to free the head and the neck or the torso of the laying patient by rotating said upper half-shell with respect to said hinge.

3. The helmet of claim 1, further comprising an airtight gasket fixed on said lower half-shell or on said upper half-shell around the circumference of the substantially spherical shape.

4. The helmet of claim 1, wherein said at least one inlet port is defined on said lower half-shell and is provided with an inlet valve.

5. The helmet of claim 1, wherein said upper half-shell comprises a handle.

6. The helmet of claim 1, wherein the helmet is made of a transparent rigid material.

7. The helmet of claim 1, wherein the at least one inlet port and/or the at least one outlet port comprises a valve configured to automatically shut upon the helmet assuming the opened position.

8. An operating table having a helmet for anesthesia, comprising:
   an operating table; and
   a helmet configured to be worn by a patient laying on the operating table,
      the helmet comprising a lower half-shell and an upper half-shell,
      the helmet further comprising an anatomically shaped portion attached to said upper half-shell and configured to form an airtight seal to a neck or a torso of the patient,
      said lower half-shell being anatomically shaped and configured to receive and support a nape and a rear part of the neck or the torso leaving free a front part of a head and of the neck or the torso and being anatomically shaped such that said lower half-shell is configured to accommodate the head of the patient laying on the operating table,
      said upper half-shell being anatomically shaped and configured to cover the front part of the head and of the neck or the torso of the laying patient,
      said upper half-shell and said lower half-shell having first fasteners for fastening said upper half-shell to said lower half-shell,
      said upper half-shell and said lower half-shell being configured to be fitted together and to the neck or the torso of the patient to form a substantially airtight enclosure configured for enclosing the head of the patient,
      said upper half-shell and said lower half-shell forming a substantially spherical shape when fitted together,
      said upper half-shell and said lower half-shell being fitted together around a circumference of the substantially spherical shape,
      said upper half-shell having an aperture closed by a flexible membrane so as to maintain the substantial airtight enclosure of the helmet, said aperture and said flexible membrane being configured to allow insertion of a laryngeal mask for patient intubation and the flexible membrane being configured to maintain the substantial airtight enclosure of the helmet by contacting the laryngeal mask,
      said upper half-shell having an annular wall formed around said aperture, said annular wall configured to fit and guide the laryngeal mask for the patient intubation,
      the helmet being configured to assume a closed position, when edges of said upper half-shell are brought to match onto corresponding edges of said lower half-shell to form a substantially airtight seal in order to prevent escape of gas, and configured to assume an opened position when said edges of said upper half-shell are detached from said corresponding edges of said lower half-shell, leaving free the front part of the head and of the neck or torso,
      wherein said upper half-shell and said lower half-shell are shaped and configured to enclose the head of the patient in said substantially airtight enclosure while surrounding the neck or the torso of the laying patient when in the closed position, and are configured to free the head and the neck or the torso of the laying patient in the opened position allowing the laying patient to exit from said lower half-shell and to remove the helmet by raising the head, or to free the head of the patient to open air without moving the head or the neck;
   the helmet further comprising second fasteners directly fixed to said lower half-shell for securing said lower half-shell to a laying surface of said operating table in a removable manner; and
   the helmet further comprising at least one inlet port for gas supply and at least one outlet port for gas evacuation being defined on said lower half-shell and/or said upper half-shell.

9. The operating table of claim 8, wherein said at least one inlet port is defined on said lower half-shell and is provided with an inlet valve.

10. The operating table of claim 8, wherein said lower half-shell is configured to constitute a headrest of the operating table.

11. The operating table of claim 8, wherein said first fasteners comprise a hinge and wherein said lower half-shell and said upper half-shell are connected by said hinge on an outside of the helmet and are configured such that the helmet is placed in the opened position to free the head and the neck or the torso of the laying patient by rotating said upper half-shell with respect to said hinge.

12. The operating table of claim 8, the helmet further comprising an airtight gasket fixed on said lower half-shell or on said upper half-shell around the circumference of the substantially spherical shape.

13. The operating table of claim 8, wherein said upper half-shell comprises a handle.

14. The operating table of claim 8, wherein the helmet is made of a transparent rigid material.

15. The helmet of claim 8, wherein the at least one inlet port and/or the at least one outlet port comprises a valve configured to automatically shut upon the helmet assuming the opened position.

\* \* \* \* \*